United States Patent
Kuo

(10) Patent No.: US 10,299,522 B2
(45) Date of Patent: May 28, 2019

(54) HUMANIZED CARE CLOTHING

(71) Applicant: Chien Chung Chen, New Taipei (TW)

(72) Inventor: Shih Huey Kuo, New Taipei (TW)

(73) Assignee: Chien Chung Chen, New Taipei (TW)

( * ) Notice: Subject to any disclaimer, the term of this patent is extended or adjusted under 35 U.S.C. 154(b) by 215 days.

(21) Appl. No.: 15/255,157

(22) Filed: Sep. 2, 2016

(65) Prior Publication Data

US 2018/0064184 A1    Mar. 8, 2018

(51) Int. Cl.
*A61F 5/37*        (2006.01)
*A41D 13/04*      (2006.01)
*A41D 13/12*      (2006.01)
*A41D 27/18*      (2006.01)

(52) U.S. Cl.
CPC ............ *A41D 13/1263* (2013.01); *A61F 5/37* (2013.01); *A61F 5/3746* (2013.01); *A41D 13/04* (2013.01); *A41D 13/129* (2013.01); *A41D 27/18* (2013.01); *A41D 2300/322* (2013.01); *A41D 2300/324* (2013.01); *A41D 2300/33* (2013.01)

(58) Field of Classification Search
CPC ......... A41B 1/02; A41B 1/06; A41B 13/0007; A41B 13/1236; A41B 13/1263; A41B 13/1245; A41B 13/1254; A44B 1/00; A44B 11/00; A61F 5/37; A61F 5/3715; A61F 5/3723; A41D 13/0007; A41D 13/1236; A41D 13/1263; A41D 13/1245; A41D 13/1254

USPC ........ 2/70, 114, 301, 265, 119, 36; 128/869, 128/873, 874, 875

See application file for complete search history.

(56) References Cited

U.S. PATENT DOCUMENTS

| 322,502 A | * | 7/1885 | Thal .......................... | A41B 1/02 2/118 |
| 344,548 A | * | 6/1886 | Schlesinger ............. | A41B 1/02 2/118 |
| 1,128,168 A | * | 2/1915 | Marcus ..................... | A41B 1/02 2/103 |

(Continued)

FOREIGN PATENT DOCUMENTS

| CA | 2800050 A1 | * | 6/2014 | ............... A41D 1/04 |
| DE | 10110178 A1 | * | 9/2002 | ......... A41D 13/1263 |

(Continued)

*Primary Examiner* — Jameson D Collier
*Assistant Examiner* — Heather N Mangine
(74) *Attorney, Agent, or Firm* — Leong C. Lei

(57) ABSTRACT

A humanized care clothing includes: a coat body, a front body thereof including left and right front side sheets spaced a full open vacancy and a detachable connecting sheet covering the vacancy, two shoulders of the connecting sheet being connectable with or detachable from two shoulder portions of a rear body, and left and right sides thereof the two opposite sides of the left and right front side sheets; a pair of restricting sleeve, two receiving pockets, two limiting pockets, a lower body clothing, the pair of buttoning sleeves being detachable from and connectable with the respective left and right front side sheets, the receiving pocket for each restricting sleeve being sewn below it, the limiting pocket being respectively overlapped with the outer parts of the receiving pockets and capable of connecting the clothing sleeve with the lower body clothing; and a collar member.

20 Claims, 6 Drawing Sheets

(56) References Cited

U.S. PATENT DOCUMENTS

| | | | | |
|---|---|---|---|---|
| 1,489,046 A * | 4/1924 | Thompson | A41B 9/08 | 2/114 |
| 2,104,487 A * | 1/1938 | Kessler | A41B 1/06 | 2/70 |
| 2,714,718 A * | 8/1955 | Kramer | A41D 15/002 | 2/265 |
| 2,725,565 A * | 12/1955 | Wyner | A41B 13/00 | 2/112 |
| 2,747,194 A * | 5/1956 | Ranieri | A41D 1/04 | 2/119 |
| 4,576,155 A * | 3/1986 | Levy | A61F 5/3723 | 128/869 |
| 4,685,454 A * | 8/1987 | Posey | A61F 5/3784 | 128/873 |
| 4,833,729 A * | 5/1989 | Fox | A41D 13/012 | 2/2.15 |
| 4,971,073 A * | 11/1990 | Schneider | A61F 5/3784 | 128/869 |
| 4,995,115 A * | 2/1991 | Ellis | A41D 13/1236 | 2/114 |
| 4,999,850 A * | 3/1991 | Grilliot | A41D 13/00 | 2/126 |
| 5,016,650 A * | 5/1991 | Marlar | A61F 5/3723 | 128/846 |
| 5,088,116 A * | 2/1992 | Gould | A41D 3/06 | 2/115 |
| 5,123,113 A * | 6/1992 | Smith | A41D 13/12 | 2/455 |
| 5,133,086 A * | 7/1992 | Truitt | A41D 13/1236 | 2/105 |
| 5,267,352 A * | 12/1993 | Rodarmel | A41D 13/1245 | 128/846 |
| 5,564,123 A * | 10/1996 | Grassick | A41D 13/1245 | 2/114 |
| 5,564,126 A * | 10/1996 | Chou | A41D 13/1245 | 2/106 |
| 5,628,064 A * | 5/1997 | Chung | A41D 15/00 | 2/119 |
| 5,652,961 A * | 8/1997 | Knight-Yurt | A41D 13/0012 | 2/106 |
| 5,799,330 A * | 9/1998 | O'Donoghue-Kitt | A41D 13/129 | 2/105 |
| 5,829,443 A * | 11/1998 | Cunningham | A61F 5/3715 | 128/869 |
| 5,991,923 A * | 11/1999 | Maria | A41D 13/1236 | 2/114 |
| 6,024,091 A * | 2/2000 | Bennett | A61F 5/37 | 128/873 |
| 6,185,745 B1 * | 2/2001 | Alger | A41B 1/06 | 2/107 |
| 6,216,271 B1 * | 4/2001 | Chen | A41D 13/1245 | 2/114 |
| 6,272,685 B1 * | 8/2001 | Kumar | A41D 13/1236 | 2/114 |
| 6,314,580 B1 * | 11/2001 | Greenberg | A41D 13/1245 | 2/108 |
| 6,393,612 B1 * | 5/2002 | Thach | A41B 13/065 | 2/69.5 |
| 6,406,449 B1 * | 6/2002 | Moore | A41D 13/1245 | 602/4 |
| 6,450,168 B1 * | 9/2002 | Nguyen | A41D 13/1272 | 128/869 |
| 6,647,552 B1 * | 11/2003 | Hogan | A41D 13/1245 | 2/114 |
| 6,935,342 B2 * | 8/2005 | Larson | A61F 5/3723 | 119/770 |
| 7,181,773 B1 * | 2/2007 | Piraka | A41D 13/1281 | 2/114 |
| 7,305,716 B1 * | 12/2007 | Richards | A41D 13/1245 | 2/114 |
| 7,454,798 B2 * | 11/2008 | Feodoroff | A41D 13/1245 | 2/114 |
| 7,954,187 B1 * | 6/2011 | Earnest | A61F 5/3723 | 2/69 |
| 8,215,313 B1 * | 7/2012 | Waltz | A61F 5/3715 | 128/849 |
| 8,566,964 B1 * | 10/2013 | Acosta | A41D 13/1245 | 2/114 |
| 8,656,516 B1 * | 2/2014 | Reinhardt Rawlings | A41D 11/00 | 2/69 |
| 8,690,835 B1 * | 4/2014 | Parris | A41D 13/1236 | 2/104 |
| 9,781,962 B2 * | 10/2017 | McClure | A41D 31/0061 | |
| 2002/0156406 A1 * | 10/2002 | Moore | A41D 13/1245 | 602/4 |
| 2004/0010837 A1 * | 1/2004 | Graves | A41D 13/1245 | 2/114 |
| 2007/0299381 A1 * | 12/2007 | Houchin | A61F 5/3723 | 602/19 |
| 2008/0053464 A1 * | 3/2008 | Wilson | A61F 5/3723 | 128/869 |
| 2008/0141432 A1 * | 6/2008 | Simon | A41D 13/1245 | 2/69 |
| 2009/0031464 A1 * | 2/2009 | Luc Gorby | A41D 13/1245 | 2/16 |
| 2009/0031471 A1 * | 2/2009 | Dague | A41D 13/1245 | 2/83 |
| 2009/0165806 A1 * | 7/2009 | Tucker | A61F 5/3715 | 128/875 |
| 2009/0217440 A1 * | 9/2009 | Sutker | A41D 13/0058 | 2/114 |
| 2011/0005525 A1 * | 1/2011 | Barnes | A61F 5/3723 | 128/845 |
| 2011/0125242 A1 * | 5/2011 | Zahler | A61F 5/3715 | 607/149 |
| 2013/0067633 A1 * | 3/2013 | Salem | A41D 13/1245 | 2/102 |
| 2015/0150317 A1 * | 6/2015 | Terrell | A41D 13/1245 | 2/114 |
| 2015/0374048 A1 * | 12/2015 | Theodossiou | A41D 13/1245 | 2/114 |
| 2016/0302497 A1 * | 10/2016 | Wu | A41D 13/1254 | |
| 2016/0324238 A1 * | 11/2016 | Tran | A41F 5/00 | |
| 2017/0007474 A1 * | 1/2017 | Kuo | A61F 13/76 | |
| 2017/0258152 A1 * | 9/2017 | Verhoeks | A41D 13/1263 | |

FOREIGN PATENT DOCUMENTS

| | | | | |
|---|---|---|---|---|
| DE | 10233706 A1 * | 2/2004 | | A41D 13/02 |
| FR | 966814 A * | 10/1950 | | A41B 1/02 |
| JP | 08060415 A * | 3/1996 | | A41D 13/1245 |
| JP | 08080319 A * | 3/1996 | | A41D 13/02 |
| JP | 2001303319 A * | 10/2001 | | A41D 13/1209 |
| WO | WO 2007056138 A2 * | 5/2007 | | A41D 13/1236 |

* cited by examiner

HUMANIZED CARE CLOTHING

(a) TECHNICAL FIELD OF THE INVENTION

The present invention relates to humanized care clothing, and more particularly to clothing suitable for patients or elders needing care.

(b) DESCRIPTION OF THE PRIOR ART

Conventional clothing such as clothes, bib, scarf or constraint object is an independent article, it has defects: 1. it leads easily to prowess, shame for elders when being worn with a bib upon eating, but if wearing no bib, the whole clothing must be changed on the occasion of vomit or food residue staining clothing 2. elders always need a scarf to keep neck warm, but the use, carrying and storage management are troublesome. 3. for dementia, restless movers or action restricted, conventional constraint objects are excessively limitative and binding, prone to resistance to gall skin, cause bad blood circulation or limb rigidity.

SUMMARY OF THE INVENTION

The object of the present invention is to provide humanized care clothing, achieving the convenience, comfort and decent appearance, reducing labor cost by integrating a bib, scarf and restraining member with clothing, and allowing them to be portable.

The present invention discloses a coat body, a front body thereof including left and right front side sheets spaced a full open vacancy and a detachable connecting sheet covering the vacancy, two shoulders of the connecting sheet being connectable with or detachable from two shoulder portions of a rear body, and left and right sides thereof the two opposite sides of the left and right front side sheets, thereby allowing the connecting sheet to be removed and replaced with a clean one quickly once it is dirty so as to maintain decent appearance any time. When the connecting sheet is removed, two shoulders thereof are removed first one by one, and the left, right sides thereof are then removed one by one, thereby preventing a human's body from being exposed and catching cold.

The present invention also discloses a pair of restricting sleeves, two limiting pockets, a lower body clothing, the pair of restricting sleeves are respectively detachable from the sides of the left and right front side sheets, and one of the receiving pockets is respectively sewn on the lower parts thereof, thereby allowing a quick operation of the restricting sleeve as the following:
1. capable of restricting an elbow softly after being put on an elbow;
2. released temporarily upon bathing, clothing changing, sleep and emotional stability, and removed forever for a person needing no more restriction;
3. removed alone for cleaning;
4. movable upward to use as a layered sleeve for keeping a upper arm warm; and
5. stored or taken to use by a user on their person.

The limiting pocket is configured on the lower part of the receiving pocket and connectable to the clothing sleeve and lower body clothing; the limiting pocket can be used simultaneously with the restricting sleeve (to restrict an elbow and palm simultaneously) or used alone; they have the following advantages:

1. restricting palm softly;
2. the receiving pocket can separate the zipper or buttons from skin, preventing it from rubbed;
3. they can be used as general pockets for keeping warm or storage; and
4. convenient for connection with the lower body clothing, allowing palms not to move upward even if the lower hem is loose.

The present invention further discloses a collar member, lower sides of head ends of front and rear surrounding sheets of the collar member being respectively sewn on left and right upper ends of a rear neckline, allowing the front and rear surrounding sheets to be engaged with each other by connecting the head and tail ends thereof to each other to surround a neck after being set upright while in use, and the front and rear surrounding sheets are respectively placed on shoulder portions while not in use the head and tail ends of front and rear surrounding sheets thereof being connected to each other to keep a neck warm; the surrounding sheets may be integrated into clothing by placing them on shoulder portions while not in use, and can be taken to use, stored, and washed with clothes any time. In addition, a conventional "stand-up collar" always causes the hot and windless feeling of a neck, but the collar member of the present invention does not. Furthermore, the collar member may have a downward extension portion facilitating hot and cold adjustment and used as a piece of mouth wiping cloth.

DETAILED DESCRIPTION OF THE PREFERRED EMBODIMENTS

Figure 1:
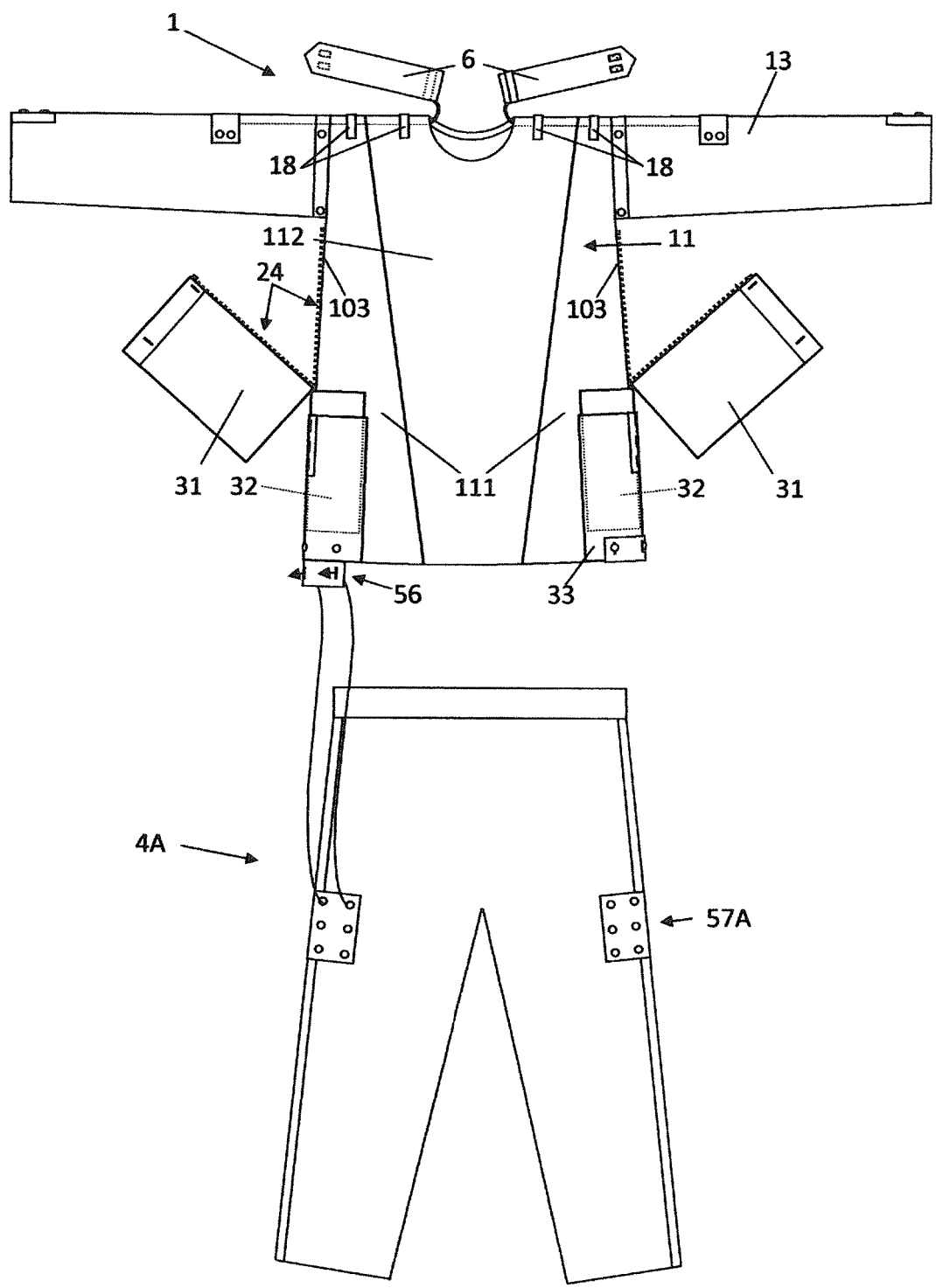
FIG. 1 is a front view of a preferred embodiment of a coat body capable of being in connection with a trousers body according to the present invention.
Figure 2:
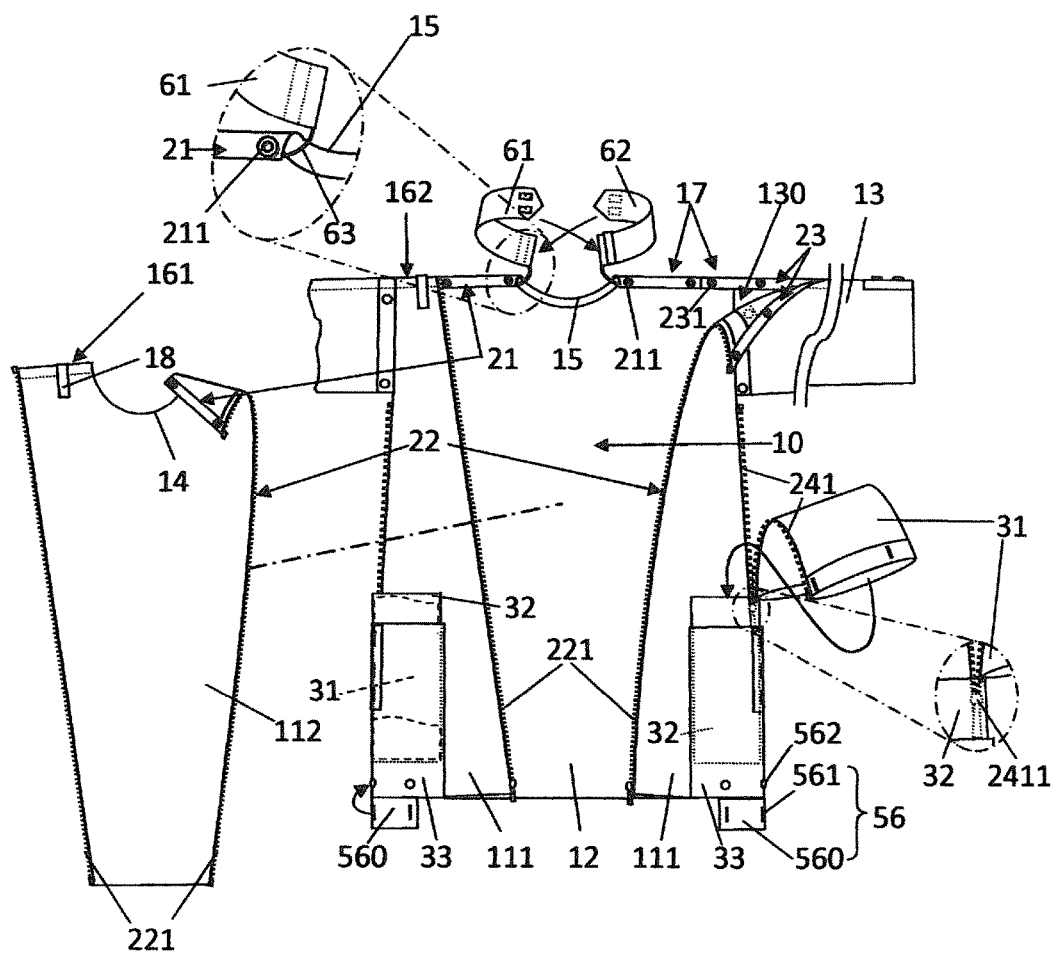
FIG. 2 is a schematic view of the embodiment of a coat body according to the present invention with a connecting sheet being removed, collar being combined and restricting sleeve being in the middle of receiving.
Figure 3:
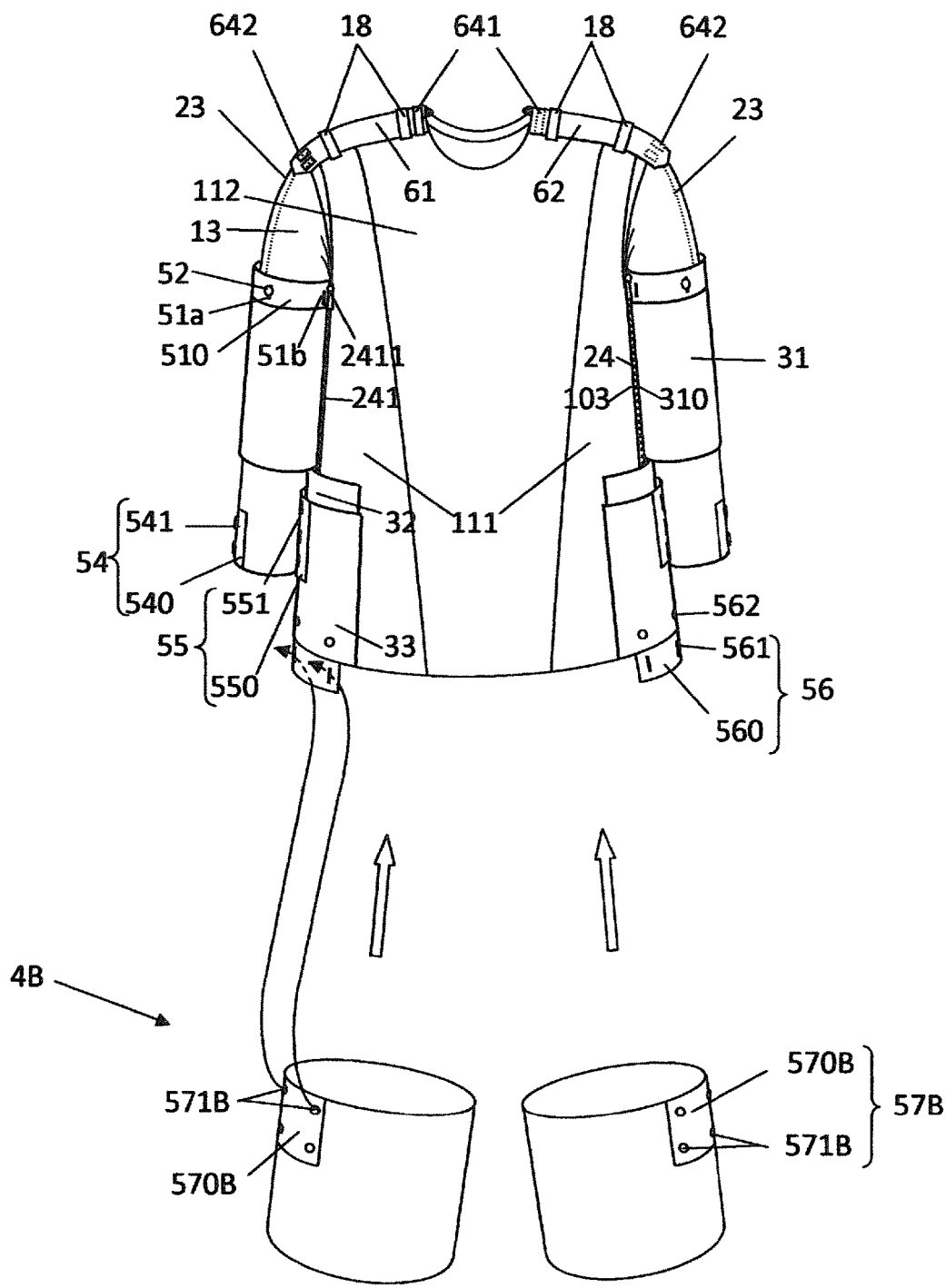
FIG. 3 is a schematic view of the embodiment of a coat body according to the present invention with a collar member being stored, and restricting sleeves being used and connected to a pair of leg sleeves.
Figure 4:
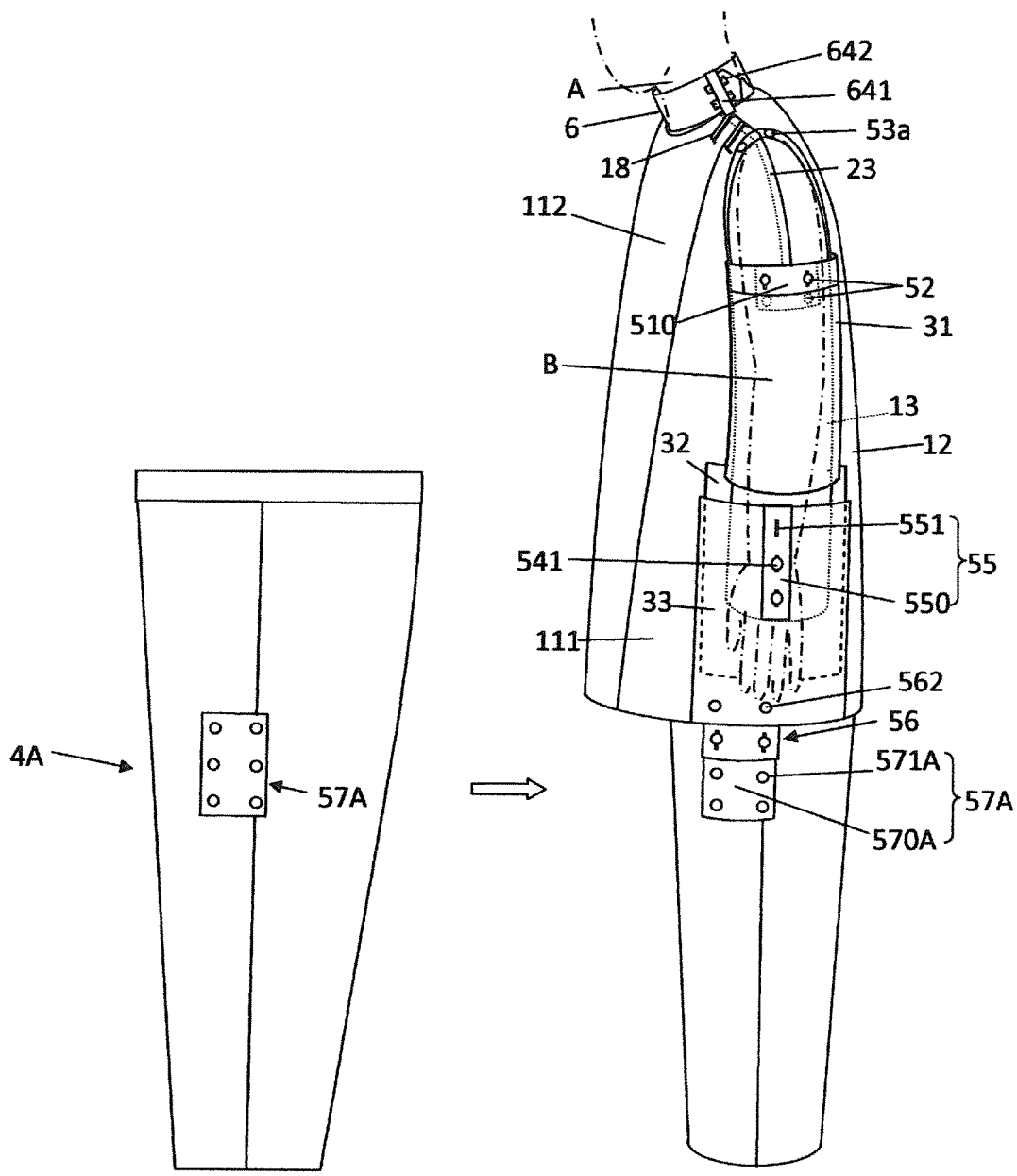
FIG. 4 is a schematic side view of the embodiment of a coat body according to the present invention with a collar member, restricting sleeves, limiting pockets and a trousers body being used at the same time.
Figure 5:
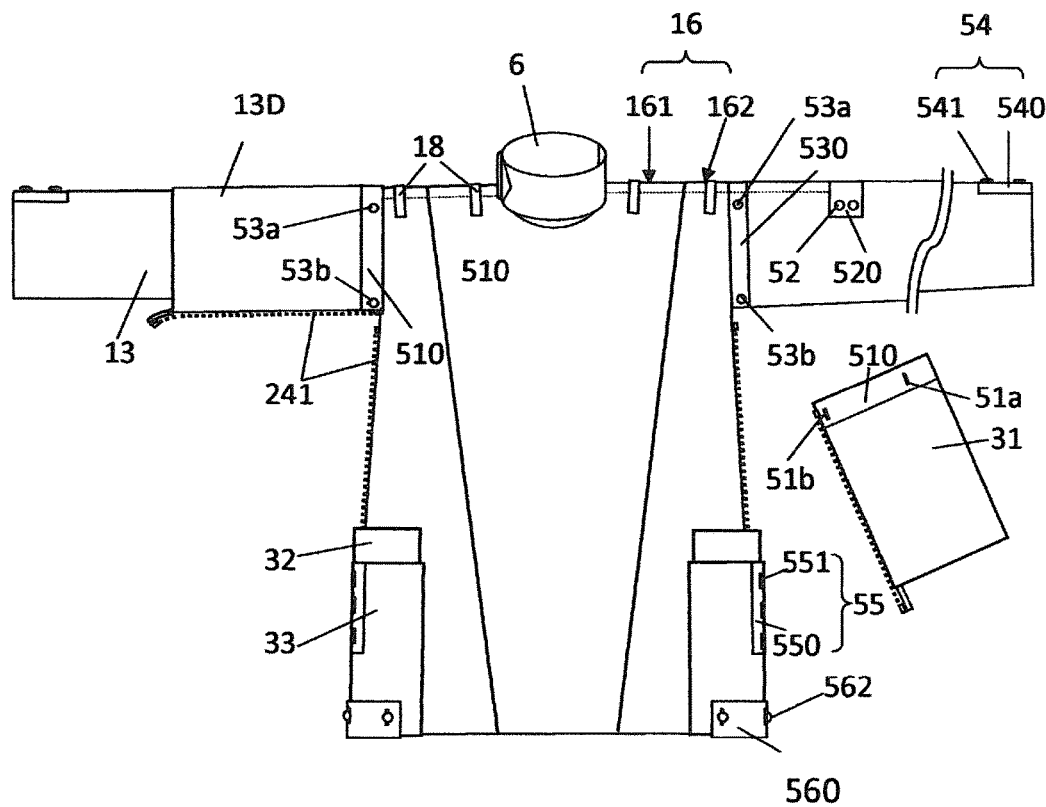
FIG. 5 is a schematic view of the embodiment of a coat body according to the present invention with a restricting sleeve being detached for cleaning and another one being moved upward to use as a layered sleeve.

Referring to FIGS. 1 and 2, humanized care clothing 1 includes a coat body, including a front body 11, rear body 12, a pair of clothing sleeves 13 with a longitudinal opening 130 respectively positioned on the upper outer sides thereof, two upper closure elements 21, two front closure elements 22 and two outer closure elements 23, where the front body 11 includes left and right front side sheets 111 spaced a fully open vacancy 10 (the ratio of top vacancy and bottom vacancy is 2:1), an in-between detachable connecting sheet 112 having a front neckline 14 and covering the vacancy 10, and the upper closure elements 21 such as male and female buckles 211 is respectively sewn between two shoulder portions 161 of the connecting sheet each occupying two thirds of shoulder width and two corresponding shoulder portions 17 of the rear body 12. Furthermore, the front closure element 22 such as a zipper 221 is respectively sewn between the left and right sides of the connecting sheet 112 and the two corresponding sides of the left, right front side sheets 111, and the outer closure element 23 such as male and female buckles 231 is respectively sewn between two shoulder portions 162 of the left, right front side sheets 111 each occupying one third of shoulder width and two corresponding shoulder portions 17 of the rear body 12 and between outward extensions thereof to each longitudinal opening 130.

Referring to FIGS. 3 to 6, the humanized care clothing of the present invention also includes a pair of restricting sleeves 31, two buttoning elements 24, two receiving pockets 32, two limiting pockets 33, a lower body clothing (trousers body 4A or leg sleeves 4B), two male, female connecting elements 54, 55 and two male, female connecting units 57A (or 57B), 56, where the buttoning element 24 such as a zipper 241, buttons 242 or male and female buckles (suitable for the one used with the limiting pocket 33) is sewn between the inner side of the restricting sleeve 31 and the corresponding side 103 of the front side sheets 111, thereby being convenient for the restriction, release, detachment and cleaning of restricting element 31. The receiving bag 32 is respectively sewn on the lower portions of the two buttoning portions 24; when the buttons or zipper head 2411 is engaged without removal (taking the restricting sleeve 31 with ease), it can be covered by the receiving pocket 32 to separate from human's skin. The upper end of each restricting sleeve 31 is configured with a plurality of buckling holes 51a close to the outer sides thereof and a buckling hole 51b close to the inner side thereof, where the buckling holes 51a allow a plurality of buttons 52 configured on the corresponding positions of the clothing sleeve 13 to be engaged therewith selectively, thereby preventing the restricting pockets from drooping. In addition, the buckling holes 51a, 51b may be engaged with and raised by a plurality of buttons 53a, 53b configured on the upper ends of each clothing sleeve 13 close to the inner and outer sides thereof to form a layered sleeve 13D.

The limiting pocket 33 is respectively overlapped with the receiving pockets 32 and sewn on the outer lower parts thereof, allowing the mouth of the receiving pocket 32 to be projected out of the limiting pocket 33 for discrimination, and a plurality of female connecting elements such as buckling holes 551 configured longitudinally on the middle of each limiting pocket 33 are adapted to be in selective engagement with a plurality of male connecting elements such as buttons 541 configured longitudinally on the corresponding positions of the outer side of the clothing sleeve 13 close to the cuff thereof.

Furthermore, a female connecting unit is respectively sewn to extend below the lower edges of the left, right front outer sides of the left, right limiting pockets, and a plurality of buckling holes 561 configured transversely on the female connecting unit are allowed to be in selective engagement with a plurality of rows of buttons 571A or 571B arranged vertically in a spaced interval on the corresponding positions of the male connecting unit 57A or 57B respectively configured on a lower body clothing such as trousers body 4A or leg sleeves 4B close to the left, right front outer sides thereof. The female connecting units 56 may be folded upward to engage with the limiting pockets 33 through buttons 562 configured on the positions thereof corresponding to the buckling holes 591 while not in use.

Figure 6:
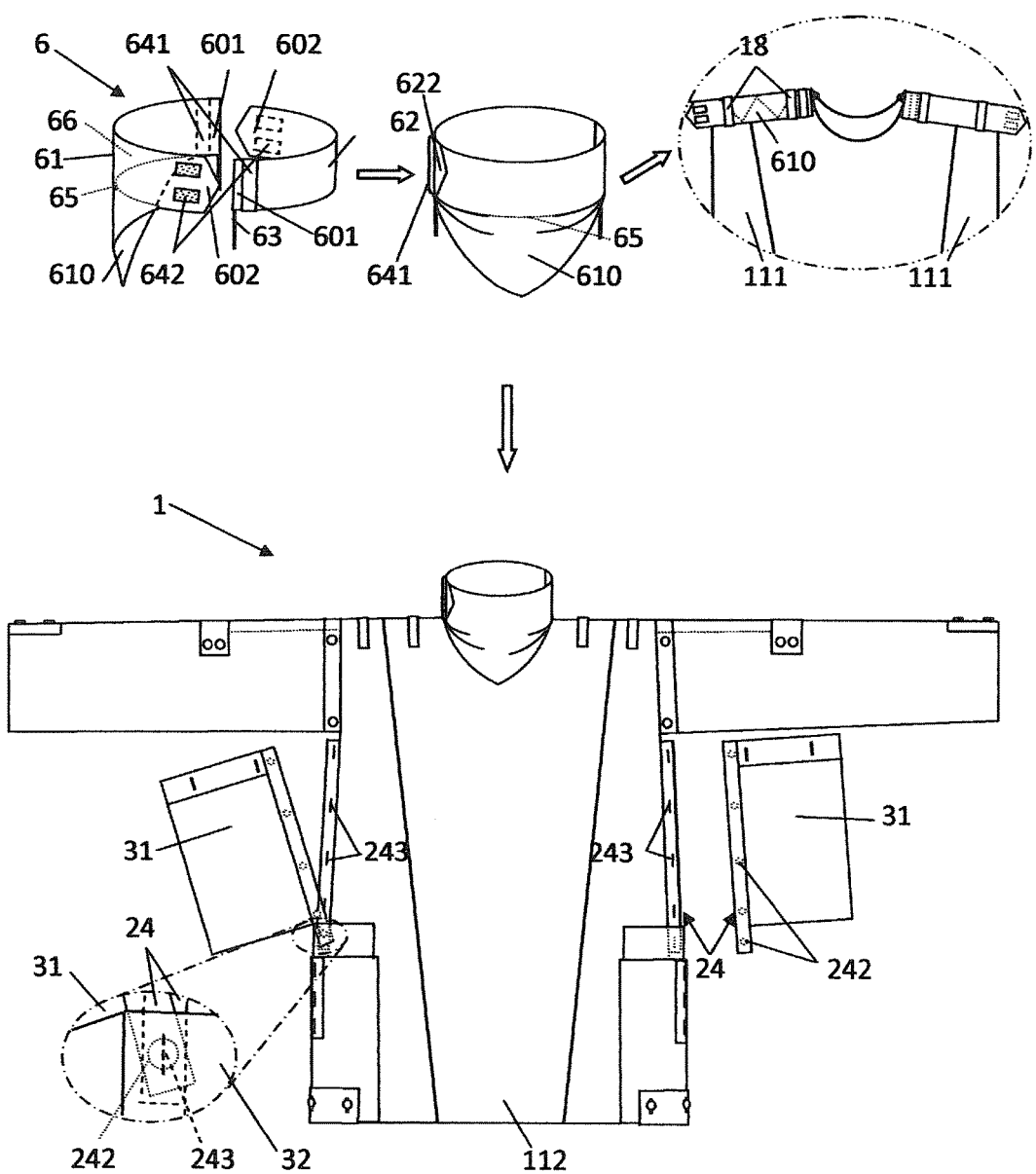
FIG. 6 is a schematic view of the embodiment of a collar member according to the present invention with a downward extension portion thereof being used and stored.

Referring to FIG. 6, a collar member 6 includes a front surrounding sheet 61 and rear surrounding sheet 62, and the lower side of each head end 601 is sewn on the left and right upper end of a front neckline 14 or rear neckline 15 through an elastic band 63; at least one male and one female fixing element such as a male part 641 of a hook and loop fastener and two female parts 642 of the hook and loop fastener are respectively configured on the head 601 end and a tail end 602, allowing the front and rear surrounding sheets 61, 62 to be engaged with each other after being set upright to surround a neck by connecting the head end of one of the surrounding sheet to the tail end of the other surrounding sheet. The two shoulder portions 16 of the front body 11 are respectively configured with a symmetrical fixing portion such as a plurality of rings 18 for accommodation, allowing the front or rear surrounding sheet 61, 62 to be passed therethrough. Furthermore, the front surrounding sheet 61 has an inverted triangle-shaped downward extension portion 610; it may be folded into an inner layer receiving space 66 through an opening 65 while not in use.

The connecting portions 510, 520, 530, 540, 550, 560, 570A, 570B may be made of tough stretch-resistant cloth so as to prevent buttons or buckling holes from being cracked or damaged due to pull and drag, where the inner layer of the connecting portions 570A, 570B and the back face of the zipper 241 may be cushioned in such a way to prevent a human body or skin from being oppressed upon lying on the side.

I claim:

1. A humanized care clothing, comprising:
   a coat body comprising a front body, a rear body directly joined to said front body, two clothing sleeves each directly joined to said front and rear bodies, wherein said two clothing sleeves are at two opposite sides of said front body and at two opposite sides of said rear body, said front body comprises a left front side sheet, a right front side sheet and a detachable connecting sheet in-between said left and right front side sheets, said detachable connecting sheet having an an uppermost edge and a lowermost edge, and wherein the uppermost edge has a greater width than the lowermost edge, two upper joining pieces each configured to join one of two shoulder portions of said detachable connecting sheet and one of two shoulder portions of said rear body, two front joining pieces each configured to join one of left and right sides of said detachable connecting sheet and an inner side of one of said left and right front side sheets, and two outer joining pieces each configured to join a shoulder portion of one of said left and right front side sheets and one of said two shoulder portions of said rear body;
   two restricting sleeves; and
   two joining elements each configured to join a longitudinal side of one of said restricting sleeves and an outer side of one of said left and right front side sheets.

2. The clothing of claim 1, wherein each of said upper joining pieces and outer joining pieces comprises a plurality of sets of male and female fasteners arranged in a spaced interval.

3. The clothing of claim 1, wherein each of said front joining pieces comprises a plurality of sets of male and female fasteners arranged in a spaced interval.

4. The clothing of claim 1, wherein each of said front joining pieces comprises a zipper.

5. The clothing of claim 1, wherein each of said joining elements comprises a zipper.

6. The clothing of claim 1, wherein each of said joining elements comprises a plurality of sets of buttons and holes for the engagement with said buttons arranged vertically in a spaced interval.

7. The clothing of claim 1, wherein each of said joining elements comprises a plurality of sets of male and female fasteners arranged vertically in a spaced interval.

8. The clothing of claim 1, wherein a ratio value of said said uppermost edge of the detachable connecting sheet to said said lowermost edge of the detachable connecting sheet is equal to 2.

9. The clothing of claim 1, wherein said one of said two shoulder portions of said detachable connecting sheet is configured to occupy two thirds of shoulder width of a wearer.

10. The clothing of claim 1, wherein said shoulder portion of said one of said left and right front side sheets is configured to occupy one third of shoulder width of a wearer.

11. The clothing of claim 1 further comprising a first receiving pocket joined to the outer side of the left front sheet and a second receiving pocket joined to the outer side of the right front sheet respectively lower than said two respective joining elements, wherein each of said receiving pockets is configured to receive one of said restricting sleeves.

12. The clothing of claim 11 further comprising a first limiting pocket joined to the outer side of the left front sheet and a second limiting pocket joined to the outer side of the right front sheet respectively, wherein said limiting pockets cover said receiving pockets respectively, two first connecting elements arranged respectively on said two limiting pockets, and two second connecting elements arranged respectively on said two clothing sleeves, wherein each of said first connecting elements is configured to join one of said second connecting elements.

13. The clothing of claim 12, wherein each of said first connecting elements comprises a hole, and each of said second connecting elements comprises a button.

14. The clothing of claim 1 further comprising a first limiting pocket joined to the outer side of the left front sheet and a second limiting pocket joined to the outer side of the right front sheet respectively, two first connecting elements arranged respectively on said two limiting pockets, and two second connecting elements arranged respectively on said two clothing sleeves, wherein each of said first connecting elements is configured to join one of said second connecting elements.

15. The clothing of claim 14, wherein each of said first connecting elements comprises a hole, and each of said second connecting elements comprises a button.

16. The clothing of claim 1 further comprising a lower body clothing configured to join said coat body, wherein said coat body comprises two first connecting units arranged below bottom edges of two respective opposite sides of said coat body, wherein said lower body clothing comprises two second connecting units at two respective opposite sides of said lower body clothing, wherein each of said first connecting units is configured to join one of said second connecting units.

17. The clothing of claim 16, wherein each of said first connecting units comprises a hole, and each of said second connecting units comprises a button.

18. The clothing of claim 16, wherein said lower body clothing comprises a pair of leg sleeves.

19. The clothing of claim 16, wherein said lower body clothing comprises a trouser body.

20. The clothing of claim 1, further comprising a collar member arranged at an upper side of said detachable connecting sheet and at an upper side of said rear body, wherein said collar member comprises a front surrounding sheet and a rear surrounding sheet, said rear surrounding sheet having two opposite ends configured to join two opposite ends of said front surrounding sheet respectively, and two elastic bands joining said front and rear surrounding sheets to said coat body respectively.

* * * * *